(12) United States Patent
Popovic et al.

(10) Patent No.: US 10,786,319 B2
(45) Date of Patent: Sep. 29, 2020

(54) SYSTEM, CONTROL UNIT AND METHOD FOR CONTROL OF A SURGICAL ROBOT

(71) Applicant: KONINKLIJKE PHILIPS N.V., Eindhoven (NL)

(72) Inventors: Aleksandra Popovic, Boston, MA (US); David Paul Noonan, New York, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 8 days.

(21) Appl. No.: 16/065,891

(22) PCT Filed: Dec. 28, 2016

(86) PCT No.: PCT/EP2016/082760
§ 371 (c)(1),
(2) Date: Jun. 25, 2018

(87) PCT Pub. No.: WO2017/114855
PCT Pub. Date: Jul. 6, 2017

(65) Prior Publication Data
US 2018/0368929 A1    Dec. 27, 2018

Related U.S. Application Data

(60) Provisional application No. 62/272,470, filed on Dec. 29, 2015.

(51) Int. Cl.
*A61B 17/00* (2006.01)
*A61B 34/30* (2016.01)
(Continued)

(52) U.S. Cl.
CPC ........ *A61B 34/30* (2016.02); *A61B 17/00234* (2013.01); *A61B 34/00* (2016.02);
(Continued)

(58) Field of Classification Search
CPC .............. A61B 34/30; A61B 17/00234; A61B 2034/2051; A61B 2034/2055;
(Continued)

(56) References Cited

U.S. PATENT DOCUMENTS 7,097,615 B2    8/2006    Banik
9,095,252 B2    8/2015    Popovic
(Continued)

FOREIGN PATENT DOCUMENTS

| EP | 2851032 A1 | 3/2015 |
|---|---|---|
| WO | 2013156893 A1 | 10/2013 |
| WO | 2014138916 A1 | 9/2014 |

*Primary Examiner* — Khoi H Tran
*Assistant Examiner* — B M M Hannan

(57) ABSTRACT

A surgical robot system is disclosed. The surgical robot system includes a handheld introducer and a flexible surgical device. A control unit includes a processor, and a memory that stores, among other things, machine readable instructions configured to be executed by a processor to control a flexible surgical device. The surgical robot system also includes an imaging device, and a tracking system. The processor is configured to generate guidance commands to control the flexible surgical device based on information relaying to the images of the flexible surgical device, and the position of at least on point of the handheld introducer.

19 Claims, 4 Drawing Sheets

(51) Int. Cl.
*A61B 34/00* (2016.01)
*A61B 34/20* (2016.01)
*A61B 90/00* (2016.01)
*A61M 25/01* (2006.01)

(52) U.S. Cl.
CPC ............... *A61B 2017/00296* (2013.01); *A61B 2017/00314* (2013.01); *A61B 2034/2046* (2016.02); *A61B 2034/2051* (2016.02); *A61B 2034/2055* (2016.02); *A61B 2034/2059* (2016.02); *A61B 2034/2063* (2016.02); *A61B 2034/2065* (2016.02); *A61B 2034/301* (2016.02); *A61B 2090/373* (2016.02); *A61B 2090/378* (2016.02); *A61B 2090/3762* (2016.02); *A61M 25/0116* (2013.01)

(58) Field of Classification Search
CPC .... A61B 2034/2059; A61B 2034/2063; A61B 2090/373; A61B 2090/3762; A61B 2090/378; A61B 2017/00296; A61B 2017/00314; A61B 2034/301; A61B 2034/2065; A61B 2034/2046; A61B 34/00; A61M 25/0116
USPC ........................................................ 700/245
See application file for complete search history.

(56) References Cited

U.S. PATENT DOCUMENTS

| | | | |
|---|---|---|---|
| 2004/0077939 A1 | 4/2004 | Graumann | |
| 2006/0258938 A1 | 11/2006 | Hoffman | |
| 2007/0021738 A1* | 1/2007 | Hasser | A61B 90/37 606/1 |
| 2007/0293734 A1* | 12/2007 | Coste-Maniere | B25J 9/1671 600/300 |
| 2008/0046122 A1* | 2/2008 | Manzo | A61B 1/00149 700/245 |
| 2011/0022060 A1* | 1/2011 | Won | A61B 34/30 606/130 |
| 2011/0040305 A1* | 2/2011 | Gomez | B25J 9/1656 606/130 |
| 2011/0282151 A1 | 11/2011 | Popovic | |
| 2012/0101508 A1* | 4/2012 | Wook Choi | B25J 9/1697 606/130 |
| 2012/0221002 A1* | 8/2012 | Long | A61B 18/12 606/45 |
| 2012/0290134 A1* | 11/2012 | Zhao | B25J 9/1689 700/259 |
| 2014/0212025 A1 | 7/2014 | Popovic | |
| 2014/0222207 A1* | 8/2014 | Bowling | A61B 34/32 700/261 |
| 2014/0358161 A1* | 12/2014 | Hourtash | A61B 34/30 606/130 |
| 2015/0010225 A1 | 1/2015 | Elhavary | |
| 2015/0073265 A1 | 3/2015 | Elhavary | |
| 2015/0126859 A1 | 5/2015 | Elhawary | |
| 2015/0202015 A1 | 7/2015 | Elhawary | |
| 2015/0366610 A1* | 12/2015 | Tsuruta | A61B 1/00029 606/46 |

* cited by examiner

User interface (screen)

SYSTEM, CONTROL UNIT AND METHOD FOR CONTROL OF A SURGICAL ROBOT

CROSS-REFERENCE TO PRIOR APPLICATIONS

This application is the U.S. National Phase application under 35 U.S.C. § 371 of International Application No. PCT/EP2016/082760, filed on Dec. 28, 2016, which claims the benefit of U.S. Provisional Patent Application No. 62/272,470, filed on Dec. 29, 2015. These applications are hereby incorporated by reference herein.

BACKGROUND

Steerable devices are often used in minimally invasive surgery to improve a surgeon's dexterity inside the patient. One known steerable device includes multiple joints and tendons at the distal end, and the drive system at the proximal end. The device can be positioned using a robotic positioner.

Another type of a steerable device used in surgery is a surgical image acquisition device, such as an endoscope, with a deflecting tip, or a robotic endoscope. Such an endoscope is a thin, elongated camera assembly that allows a clinician to view the internal anatomy of a patient without the need to surgically expose the anatomy for a direct view. Endoscopes can fit through narrow natural orifices or small incisions in the skin, resulting in reduced trauma to the patient as compared to visualization and intervention without the aid of an endoscope.

Control of known dexterous devices is challenging, especially when the device is used in connection with a handheld introducer. Handheld introducers can be used to place, orient, position and introduce the flexible device within a patient. When using a flexible device in conjunction with a handheld introducer, the user has to combine the motion of handheld introducer, which is usually pivoting about an entry point to the body with complex dexterous motion of the flexible device inside the body. One approach to this problem is robotic positioning of the dexterous device. This however increases the footprint of the system in the operating room and increases cost and duration of surgery. In addition, once the position is achieved with the dexterous device, hand tremors and involuntary motion of the hand can cause misalignment.

Accordingly, it may be desirable to provide an apparatus, systems, methods, and computer-readable storage medium for control of a flexible surgical device that monitors the handheld introducer using a combination of medical imagery and tracking information to correct for misalignment.

SUMMARY

According to a representative embodiment, a surgical robot system comprises a flexible surgical device; a handheld introducer configured to facilitate the introduction of the flexible surgical device; and an imaging device configured to capture one or more images of the flexible surgical device and/or patient anatomy. The images from the imaging device are indicative of at least one of: the shape, pose, and position of the flexible surgical device. The surgical robot system further comprises a tracking system configured to track the position of at least one point on the handheld introducer; and a processor configured to generate guidance commands to control the flexible surgical device based on information relating to the images of the flexible surgical device and the position of at least one point of the handheld introducer.

Accordance to another representative embodiment, a control unit for a surgical robot system comprises a flexible surgical device and a handheld introducer configured to facilitate the introduction of the flexible surgical device. The control unit further comprises: a processor configured to: receive, from an imaging device, one or more images of the flexible surgical device, the images being indicative of at least one of: the shape, pose, and position of the flexible surgical device; receive, from a tracking system, tracking information indicative of the position of at least one point on the handheld introducer; and generate guidance commands to control the flexible surgical device based on information relating to the images of the flexible surgical device and the position of at least one point of the handheld introducer.

According to another representative embodiment, a non-transitory computer-readable storage medium has stored therein machine readable instructions configured to be executed by a processor to control a flexible surgical device and a handheld introducer configured to facilitate the introduction of the flexible surgical device at a surgical site. The machine readable instructions are configured to perform a method to compensate for motion of the rigid portion. The method comprises receiving, from an imaging device, one or more images of the flexible surgical device. The images are indicative of at least one of: the shape, pose, and position of the flexible surgical device. The method further comprises receiving, from a tracking system, tracking information indicative of the position of at least one point on the handheld introducer; and generating guidance commands to control the flexible surgical device based on information relating to the images of the flexible surgical device and the position of the at least one point of the handheld introducer.

BRIEF DESCRIPTION OF THE DRAWINGS

The representative embodiments are best understood from the following detailed description when read with the accompanying drawing figures. It is emphasized that the various features are not necessarily drawn to scale. In fact, the dimensions may be arbitrarily increased or decreased for clarity of discussion. Wherever applicable and practical, like reference numerals refer to like elements.

DETAILED DESCRIPTION

Figure 1A:
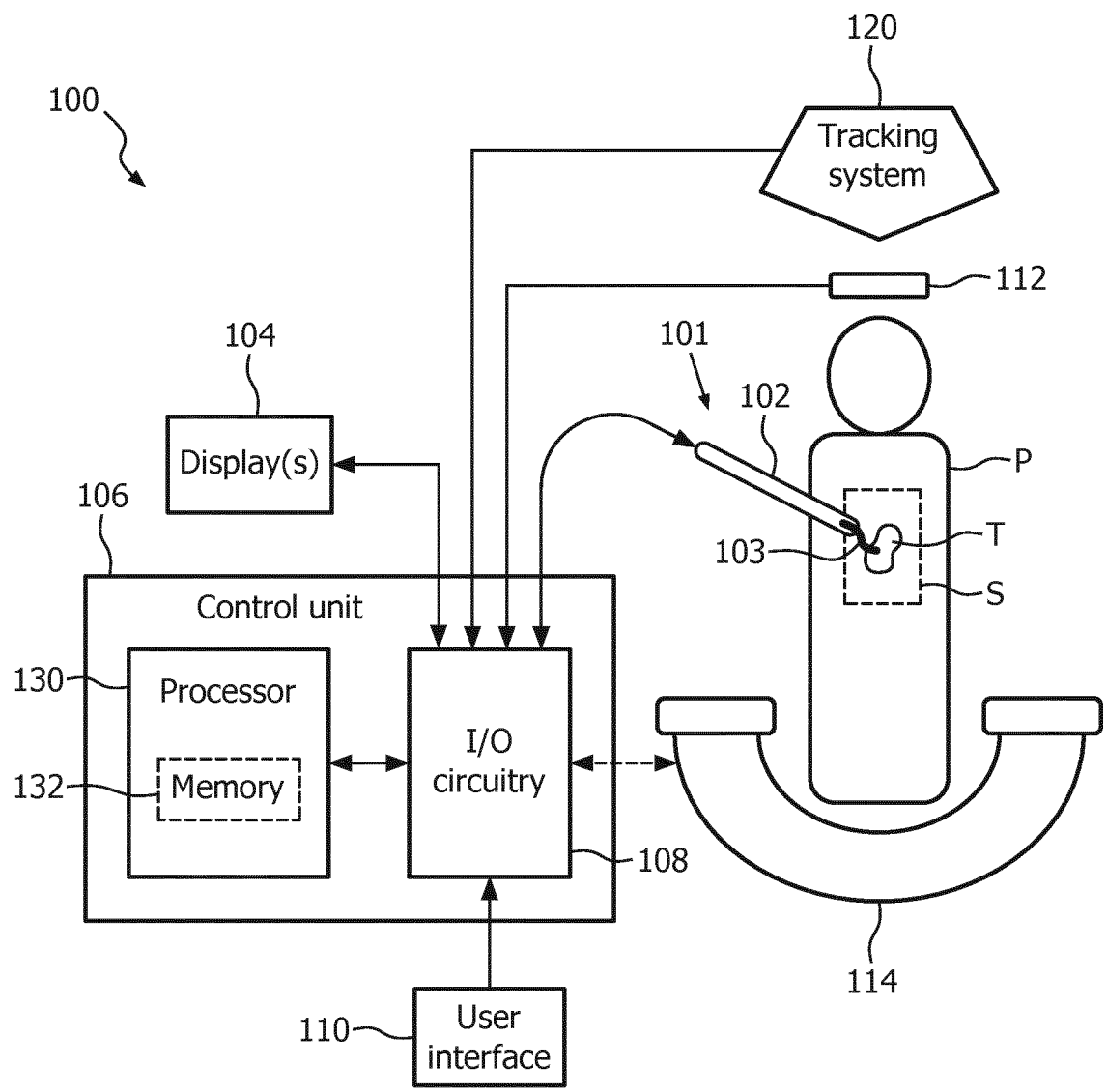
FIG. 1A is a schematic block diagram illustrating a surgical robot system in accordance with features of a representative embodiment.

In the following detailed description, for purposes of explanation and not limitation, representative embodiments disclosing specific details are set forth in order to provide a thorough understanding of the present teachings. However, it will be apparent to one having ordinary skill in the art having had the benefit of the present disclosure that other embodiments according to the present teachings that depart from the specific details disclosed herein remain within the scope of the appended claims. Moreover, descriptions of well-known apparatuses and methods may be omitted so as to not obscure the description of the representative embodiments. Such methods and apparatuses are clearly within the scope of the present teachings.

It is to be understood that the terminology used herein is for purposes of describing particular embodiments only, and is not intended to be limiting. Any defined terms are in addition to the technical and scientific meanings of the defined terms as commonly understood and accepted in the technical field of the present teachings.

As used in the specification and appended claims, the terms 'a', 'an' and 'the' comprises both singular and plural referents, unless the context clearly dictates otherwise. Thus, for example, 'a device' includes one device and plural devices.

As used herein, the statement that two or more parts or components are "coupled" shall mean that the parts are joined or operate together either directly or indirectly, i.e., through one or more intermediate parts or components, so long as a link occurs.

Directional terms/phrases and relative terms/phrases may be used to describe the various elements' relationships to one another, as illustrated in the accompanying drawings. These terms/phrases are intended to encompass different orientations of the device and/or elements in addition to the orientation depicted in the drawings.

Relative terms, such as "above," "below," "top," "bottom," "upper" and "lower" may be used to describe the various elements' relationships to one another, as illustrated in the accompanying drawings. These relative terms are intended to encompass different orientations of the device and/or elements in addition to the orientation depicted in the drawings. For example, if the device were inverted with respect to the view in the drawings, an element described as "above" another element, for example, would now be "below" that element. Similarly, if the device were rotated by 90° with respect to the view in the drawings, an element described "above" or "below" another element would now be "adjacent" to the other element; where "adjacent" means either abutting the other element, or having one or more layers, materials, structures, etc., between the elements.

As used in the specification and appended claims, and in addition to their ordinary meanings, the terms 'substantial' or 'substantially' mean to with acceptable limits or degree. For example, 'substantially cancelled' means that one skilled in the art would consider the cancellation to be acceptable.

Referring initially to FIG. 1A, a surgical robot system 100 in accordance with features of the present teachings will be described. In particular, the surgical robot system 100 may be utilized for medical procedures including, but are not limited to, minimally invasive cardiac surgery, including, but not limited to: coronary artery bypass grafting, and mitral valve replacement; minimally invasive abdominal surgery, such as laparoscopy to perform prostatectomy or cholecystectomy; and natural orifice translumenal endoscopic surgery, for example.

FIG. 1A schematically illustrates the surgical robot system 100 comprising a surgical robot 101 having a flexible surgical device 103 guided to and positioned at a surgical site S within a patient's body P, and a handheld introducer 102 to facilitate the introduction into a surgical patient of the flexible surgical device 103.

As will be clearer as the present description continues, the handheld introducer 102 is configured for manual movement along a number of degrees of freedom. To this end, the handheld introducer 102 is manually manipulated by the clinician for guiding the flexible surgical device 103 to the desired target location T. As described more fully below, in accordance with the present teachings, movement of the handheld introducer 102 is tracked, and based in part on this movement, the control commands to the flexible surgical device 103 can be adjusted to ensure accurate location of the flexible surgical device 103 relative to the target location T. The handheld introducer 102 illustratively comprises a tubular portion (not shown) through which components useful in effecting the particular surgical procedure can be guided. By way of example, the flexible surgical device 103, imaging devices (e.g., endoscopes), end-effectors, and other components (e.g., heart valves or stents) can be fed through the handheld introducer 102.

In certain embodiments, the surgical robot system 100 comprises a display 104, which is capable of providing real-time images of the location of the flexible surgical device 103, as described more fully below.

Generally, the flexible surgical device 103 comprises at least two links, and at least one joint therebetween. As described more fully below in connection with representative embodiments, the surgical robot 101 is structurally configured to control one or more joints of the flexible surgical device 103 for maneuvering the flexible surgical device 103 which has one or more degrees of freedom.

Illustratively, the flexible surgical device 103 may be one of a number of devices, including but not limited to a two-linkage, one joint device, a snake-like robot, or a steerable catheter. In practice, as would be appreciated by those skilled in the art, the flexible surgical device 103 is configured to move in one or more degrees of freedom. More generally, the flexible surgical device 103 may have five (5) or six (6) degrees-of-freedom.

By way of example, in certain embodiments, the flexible surgical device 103 comprises a plurality of links and joints, which are controlled as discussed below to properly locate an end 103' of the flexible surgical device 103 in a desired location (e.g., at a target). One such multiple link, multiple joint device is depicted in FIG. 1B.

Figure 1B:
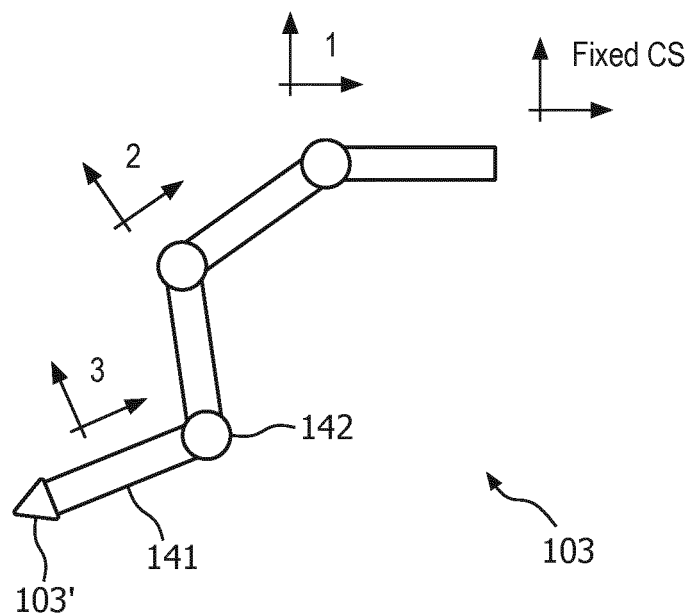
FIG. 1B is a perspective view of a flexible surgical device of a surgical robot in accordance with a representative embodiment.

Referring to FIG. 1B, the flexible surgical device 103 of a representative embodiment comprises a plurality of links 141, each connected by a respective joint 142. Each of the plurality of links comprises a rigid segment, and each of the joints 142 may comprise a geared assembly. Illustratively, each joint 142 can implement between one and three degrees of freedom (roll, pitch, and yaw). As described more fully below, a control unit 106 is configured to perform motor control and collect position and orientation data of the flexible surgical device 103.

Alternatively, the flexible surgical device may be a snake robot, such as described in U.S. Pat. No. 7,097,615, the disclosure of which is specifically incorporated herein by reference. As will be appreciated, the flexible surgical device 103 may comprise an end-effector (not shown) as desired for the particular robotic procedure. By way of example, the end-effector connected to the flexible surgical device 103 may comprise a gripper or a tool holder. Similarly, the flexible surgical device 103 may comprise a tool such as a laparoscopic instrument, laparoscope, a tool for screw placement, or a needle for biopsy or therapy. Other surgical devices and tools within the purview of one of ordinary skill in the art are also contemplated to be used with the flexible surgical device 103.

In certain embodiments, the display 104 comprises an output device, or a user interface, or both adapted for displaying images or data, as described more fully herein. The display 104 may include one or more displays that may be co-located near the clinician positioned adjacent to various elements of the surgical robot system 100. The display 104 is configured to display live or preoperative images of the surgical site S.

A display may output visual, audio, and or tactile data. Examples of a display include, but are not limited to: a computer monitor, a television screen, a touch screen, tactile electronic display, Braille screen, Cathode ray tube (CRT), Storage tube, Bistable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

The control unit 106 is configured to receive input from various components of the surgical robot system 100, and to provide outputs thereto, as is described more fully below. In certain embodiments, a control unit 106 comprises input/output (I/O) circuitry 108, which receives inputs from various components of the surgical robot system 100, and provides output to and receives inputs from a processor 130, as is described more fully below. The processor 130 also comprises a memory 132.

The processor 130 may comprise one or more microprocessors that may be programmed using software (e.g., microcode) to perform various functions discussed herein. Notably, the processor 130 may comprise more than one processor or processing core. The processor 130 may for instance be a multi-core processor. The processor 130 may also comprise a collection of processors within a single computer system (not shown) or distributed among multiple computer systems (not shown) associated with the surgical robot system 100. As will be appreciated as the present description continues, many programs have their instructions performed by the processor 130 that may be within the same computing device or which may even be distributed across multiple computing devices.

Examples of components that may be employed as the processor 130 in various embodiments of the present disclosure include, but are not limited to, conventional microprocessors, microcontrol units, application specific integrated circuits (ASICs), and field-programmable gate arrays (FPGAs).

The memory 132 is configured to store various types of data gathered during the course of the function of the various components of the surgical robot system 100. These data include image data and tracking data gathered as described more fully below. The memory 132 may also store pre-operative data, such as pre-operative image data. As described more fully below, these data can be used to track the location of the flexible surgical device 103 during operation. Furthermore, the memory 132 comprises a non-transitory computer readable medium, which stores machine readable instructions configured to be executed by the processor 130 to control the surgical robot system 100. By way of example, these instructions (programs) are encoded in the memory 132, and when executed on the processor 130, perform at least some of the functions discussed herein. Notably, the terms "program" or "computer program" are used herein in a generic sense to refer to various types of computer code (e.g., software or microcode) that can be employed to program the control unit 106.

The memory 132 may comprise non-volatile computer memory, or volatile computer memory, or both, including, but not limited to: such as random-access memory (RAM), read-only memory (ROM), programmable read-only memory (PROM), electrically programmable read-only memory (EPROM), electrically erasable and programmable read only memory (EEPROM), universal serial bus (USB) drive, floppy disks, compact disks (CDs), optical disks, magnetic tape, etc.), a smart card, a digital video disc (DVD), a CD-ROM, and a solid state hard drive. Various storage media may be fixed within the processor 130 or may be transportable, such that the one or more programs stored thereon can be loaded into the processor 130 so as to implement various aspects of the present teachings discussed herein.

The surgical robot system 100 further comprises an image acquisition device 112. The image acquisition device 112 may be configured to acquire a live image or live images of the flexible surgical device 103 of the surgical robot 101 and an anatomical object, such as an organ or other target location T at the surgical site S.

Generally, the image acquisition device 112 may comprise one of a variety of inter-operative imaging devices within the purview of one of ordinary skill in the art to provide real-time imaging. Contemplated imaging devices for the image acquisition device 112 include, but are not limited to an endoscope, a C-arm X-ray device, computed tomography (CT) devices, ultrasound imaging devices, magnetic resonance imaging (MRI) devices, positron emission tomography (PET) devices, single-photon emission computed tomography (SPECT) imaging devices.

Notably, the image acquisition device 112 is depicted near the patient P. Of course, the actual location of the image acquisition device 112 depends on the type of device that is used. For example, and as noted below, if an endoscope or similar device were used, the image acquisition device 112 may be located inside the patient P, such as an attachment to the flexible surgical device 103. Alternatively, if the image acquisition device were a C-arm X-ray device, the image acquisition device 112 would be located with a C-arm 114, which is an imaging scanner intensifier, so named because of its C-configuration. C-arms have radiographic capabilities, and may be used for fluoroscopic imaging during surgical procedures, as is known to those skilled in the art.

In the representative embodiments described below, the image acquisition device 112 may comprise an endoscope, which provides endoscopic images. The endoscope (not shown) may be a component of, or connected to, the flexible surgical device 103. In certain representative embodiments, the endoscope may include a rigid or flexible tube, and a light delivery system to illuminate the organ or object under inspection, for example, the light source is normally outside the body and the light is typically directed via an optical fiber system. Also included may be a lens system transmitting the image from the objective lens to the viewer, typically a relay lens system in the case of rigid endoscopes or a bundle of fiberoptics in the case of a fiberscope. Also contemplated are videoscopes, with no eyepiece, in which a camera transmits images to a screen for image capture. An additional channel may allow entry of medical instruments or manipulators. It is emphasized that the use of an endoscope as the image acquisition device 112 is merely illustrative, and other devices, such as those noted above, are contemplated for use as the image acquisition device 112.

The term "endoscopic" is broadly defined herein as a characterization of images acquired by one or more of a variety of endoscopes having the ability to image from inside a body. Examples of an endoscope for purposes of the present teachings include, but are not limited to, any type of scope, flexible or rigid (e.g., endoscope, arthroscope, bronchoscope, choledochoscope, colonoscope, cystoscope, duodenoscope, gastroscope, hysteroscope, laparoscope, laryngoscope, neuroscope, otoscope, push enteroscope, rhinolaryngoscope, sigmoidoscope, sinuscope, thorascope, etc.) and any device similar to a scope that is equipped with an image system. The imaging is local, and surface images may be obtained optically with fiber optics, lenses, or miniaturized (e.g. CCD based) imaging systems. Further details of an endoscopic system contemplated for use in connection with the present teachings may be found, for example, in commonly-owned U.S. Patent Application 20140301618, the disclosure of which is specifically incorporated herein by reference.

The image acquisition device 112 is connected to, and may be a component of the control unit 106. The image acquisition device 112 provides images ultimately provided to the display 104, and may include any type of camera having a forward optical view or an oblique optical view, and may be capable of acquiring a sequence of two-dimensional digital video frames at a predefined frame rate (e.g., 30 frames per second) and capable of providing each digital video frame to the control unit 106 via the I/O circuitry 108. In particular, image acquisition device 112 may be positioned and oriented such that within its field of view it can capture images of the flexible surgical device 103. In some embodiments, image acquisition device 112 includes a camera which is actuated by a motor and it can be positioned along a planned instrument path for surgical robot 101.

Because a surgical robot 101, with or without an endoscope, introduces an additional coordinate system, alignment (position and orientation) of the surgical robot 101 with some desired frame of reference is difficult to guarantee and maintain because it is positioned with workspace and motion constraints. As described more fully below, misalignment of disparate coordinate systems so that the same alignment need not be performed mentally by clinicians is effected using known registration methods and apparatuses. To this end, variety of current methods and apparatuses exist to register a surgical robot 101 and the particular components thereof to the imaging system. By way of example, registration can be performed by matching features of the flexible device visible in the images with corresponding features gathered preoperatively. The target location T can be identified by the surgeon by marking the location of T in the images. In another embodiment, the target location T can be automatically detected by means of feature matching and object recognition known in art. The target location T can then be computed from the image to the robot coordinate system using registration.

Illustratively, registration to ensure proper alignment of the flexible surgical device 103 are described in one or more of commonly owned U.S. Pat. No. 9,095,252; and U.S. Patent Application Publications 20110282151, 20140212025, 20150010225, 20150073265, 20150126859, and 20150202015. The entire disclosures of this U.S. Patent, and these U.S. Patent Application Publications are specifically incorporated herein by reference.

A tracking system 120 is configured to generate tracking information with respect to the handheld introducer 102 of the surgical robot 101. The tracking system 120 may be one or more of an optical tracking system, mechanical tracking system, and electromagnetic tracking system, as would be appreciated by those skilled in the art. A sensor or tag, such as a radio frequency (RF) sensor, LED sensor, passive markers, reflective markers, could be included at the handheld introducer 102 of the surgical robot 101, or proximal to the end 103' of the flexible surgical device 103, or both to cooperate with the tracking system 120.

The tracking system 120 provides information to the control unit 106 to provide feedback of the current position of the handheld introducer 102, and thereby the flexible surgical device 103, allowing adjustment of the position of the flexible surgical device 103 relative to the target location T. Through tracking of the handheld introducer 102 and data from the registration realized by the image acquisition device 112, the processor 130 is configured to determine the location of the flexible surgical device 103 relative to the target location T. Notably, software in the memory 132 enables the calculation by the processor of the current location of the flexible surgical device 103 relative to the target location T, and calculates required commands to effect a desired movement of the flexible surgical device. Based on these calculations, the processor 130 provides instructions (sometimes referred to herein as commands, control commands, guidance commands, or guidance signals) to the flexible surgical device 103 to move as needed to be in better position relative to the target location T. As described more fully below, in some embodiments, these commands are used in position guidance mode to aide the clinician in guiding the handheld introducer, and flexible surgical device 103 (and any end-effector, or device attached thereto) to a particular location in the patient P. In other embodiments described below, in position compensation mode these commands function to compensate for (i.e., substantially nullify) any undesired movement by the flexible surgical device 103. For example, the undesired movement of the flexible surgical device 103 may be caused by tremor-induced motion in the handheld introducer 102. As such, in position compensation mode, any undesired motion cause by tremor can be substantially nullified by providing commands to counter the undesired induced motion.

In certain embodiments, the surgical robot system 100 comprises a user interface 110. The user interface 110, like the display 104, is illustratively coupled to the control unit 106 via a hardware interface (not shown) and the I/O circuitry 108. The hardware interface enables the processor 130 to interact with various components of the surgical system, as well as control an external computing device (not shown) and/or apparatus. The hardware interface may allow a processor to send control commands or instructions to various components of the surgical system, as well as an external computing device and/or apparatus. The hardware interface may also enable a processor to exchange data with various components of the surgical system, as well as with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

The user interface 110 allows the clinician to interact with surgical robot system 100 through a computer (not shown) or computer system (not shown). The user interface 110 comprises, for example, a touch screen, a keyboard, a mouse, a trackball or touchpad. Generally, the user interface 110 may provide information or data to the clinician and/or receive information or data from the clinician. The user interface 110 may be configured to receive input from the clinician to be received by the computer, and may provide output to the user from the computer. In other words, and as will become clearer as the present description continues, the user interface 110 may be configured to enable the operator to control or manipulate the computer, and the user interface 110 may be configured to allow the computer to indicate the effects of the clinician's control or manipulation. The display of data or information on the display 104 or a graphical user interface thereof, is an example of providing information to the clinician. The receiving of data through a touch screen, keyboard, mouse, trackball, touchpad, pointing stick, graphics tablet, joystick, gamepad, webcam, headset, gear sticks, steering wheel, wired glove, wireless remote control, and accelerometer are all examples of components of the user interface 110, which enable the receiving of information or data from an operator.

As noted above, the control unit 106 may comprise I/O circuitry 108. Among other functions, I/O circuitry 108 controls communication to elements and devices external to the control unit 106. The I/O circuitry 108 acts as an interface including necessary logic to interpret input and output signals or data to/from the processor 130. The I/O circuitry 108 may include a first input configured to receive the medical imagery, such as from the image acquisition device 112 related to the flexible surgical device 103 of the surgical robot 101 at the surgical site S, and a second input configured to receive the tracking information of the handheld introducer 102 of the surgical robot 101 from the tracking system 120. The I/O circuitry 108 may include an output configured to provide the medical imagery related to the flexible surgical device 103 of the surgical robot 101 to the display 104.

The processor 130 may perform the described functions and operations using a combination of hardware, software and firmware. The processor 130 is configured to process images, related to the flexible surgical device 103 of the surgical robot 101 at the surgical site S. In certain embodiments, the processor 130 registers the flexible surgical device 103 with corresponding anatomy at the surgical site S. As described in connection with FIG. 2, the processor 130 is configured to process the tracking information of the handheld introducer 102 of the surgical robot 101 from the tracking system 120 to determine motion of the handheld introducer 102. In a position compensation mode, the processor 130 is configured to generate motion compensation commands for the flexible surgical device 103 of the surgical robot 101 based upon the determined motion of the handheld introducer 102.

In certain embodiments, the processor 130 may be further configured to transmit the images related to the flexible surgical device 103 of the surgical robot 101 to the display 104 via the I/O circuitry 108.

As can be appreciated from the description above, in certain embodiments, through the coordinated function of the image acquisition device 112, the tracking system 120, the various data and software stored in memory 132, and the actions of the processor 130, the control unit 106 is configured to provide one or more control commands to control the acquisition and processing of live and preoperative images related to the flexible surgical device 103 of the surgical robot 101 at the surgical site S, and the anatomical object or target T, and use tracking information related to the handheld introducer 102 of the surgical robot 101 to further control the flexible surgical device 103 relative to the target location T. In the illustrative examples described below, various features of the surgical robot system 100 of representative embodiments are further described. It is noted that these examples are merely illustrative, and in no way intended to be limiting.

Figure 2:
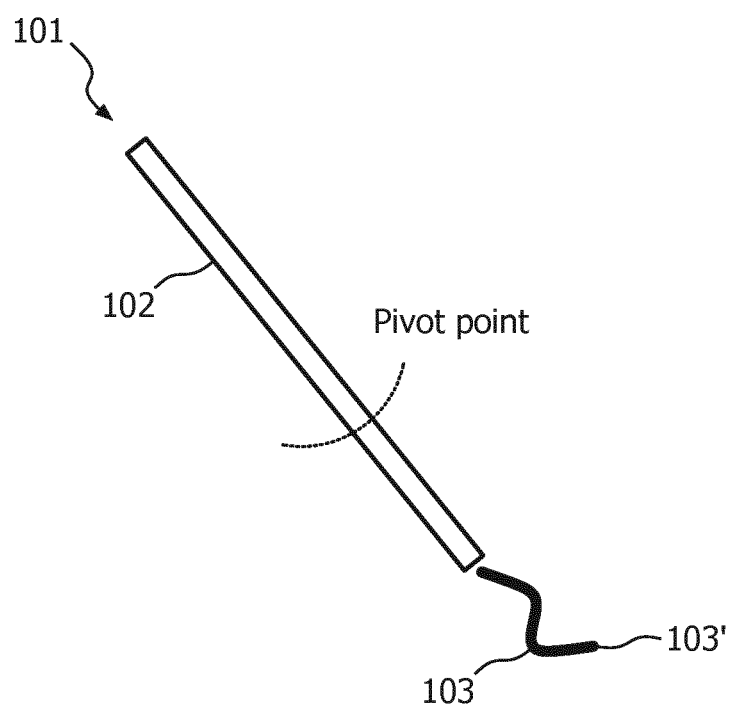
FIG. 2 is a schematic diagram illustrating details of surgical robot of the system of FIG. 1A.
Figure 3:
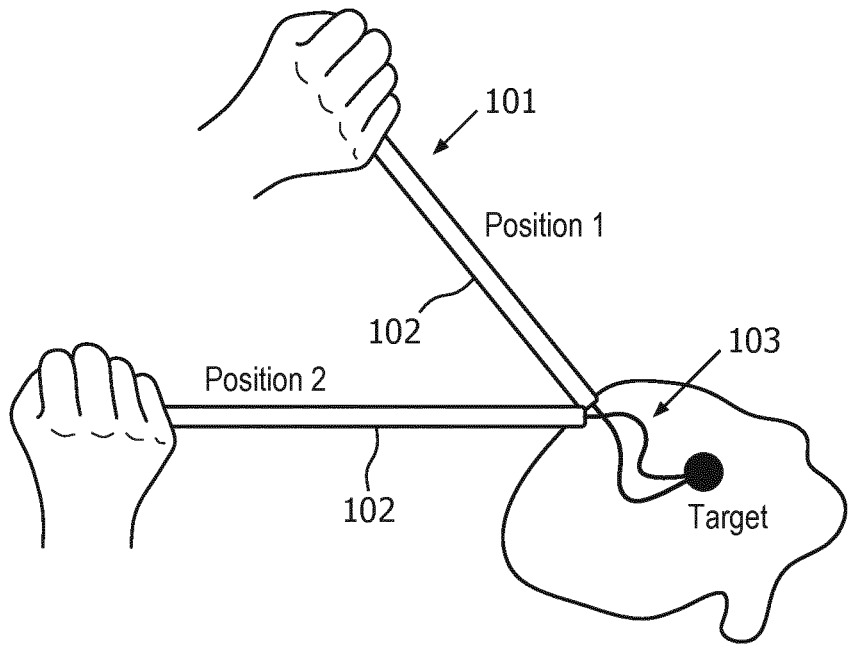
FIG. 3 is a schematic diagram illustrating a compensation mode of the surgical robot of the system of FIG. 1A.

With additional reference to FIGS. 2-4B, the surgical robot 101 is flexible and inserted into the patient through a surgical port. In the present illustrative example, the surgical robot 101 is used to place a valve in a heart (not shown) of patient P at target location T. As such, an initial incision is made between two ribs to provide the surgical port. This handheld introducer 102 pivots around the surgical port ("pivot point") as depicted in FIG. 2.

Next, the flexible surgical device 103 moves inside the patient's cavity without injuring the entry point. As noted above, movement of the handheld introducer 102 is tracked by the tracking system 120. Using data from the tracking system 120 alone, or in combination with data from the image acquisition device 112, the processor 130 calculates the impact of movement of the handheld introducer 102 on the flexible surgical device 103, and especially the end 103' thereof. As noted above, based on at least some of these data, the processor 130 can provide commands to the flexible surgical device 103 of the surgical robot 101 to adjust its position relative to the target location T.

In certain embodiments, the position of the end 103' is determined by the clinician by images provided at the display 104. As such, an end effector disposed at the end 103' can be used to make an incision at a precise location of the heart muscle. The clinician can then further guide the end 103' of the flexible surgical device 103 to the location of the valve to be replaced. The valve can then be replaced, again with the precision location of the target T being determined by the control unit 106 using the various image acquisition and registration methods described above.

Based on data from the tracking system 120 alone, or in combination with data from the image acquisition device 112, the processor 130 can compensate for sporadic movement (e.g., induced by clinician tremor) of the handheld introducer 102 through commands to the flexible surgical device 103 of the surgical robot 101 so that substantially nullifying movement of the flexible surgical device 103 can negate the tremor at the end 103' of the flexible surgical device 103.

In a representative embodiment, in a position compensation mode, an image related to the flexible surgical device 103 is taken using the image acquisition device 112. As noted above, the image may be an X-ray image, cone-beam CT image, an ultrasound image, or an endoscopic image. The shape and pose of the flexible surgical device 103, and/or registration within the surgical site S, is thereby determined and may be shown on the display 104. For example, real-time tracking of surgical tools relative to a pre-operative surgical plan and interoperative images involving an image-based registration and tool tracking registration are disclosed in above-referenced U.S. Patent Application Publications. Since anatomy is visible in the image, the relative position of the flexible surgical device 103 with respect to the anatomy is also known, and the flexible surgical device 103 can be used to reach the anatomical target T (in this example the location of the valve to be replaced) using the position computed by the control unit 106. In order to keep the flexible surgical device 103 in the same position for the duration of procedure, such as biopsy or heart ablation, in a manner described above, the control unit 106 continually or continuously updates the position of the handheld introducer 102 of the surgical robot 101 from the tracking system 120 using tracking information from the tracking system 120, and possibly the image acquisition device 112.

In a representative embodiment, control unit 106 may compute surgical robot 101 motion parameters of joints (e.g., joints 142) of the flexible surgical device 103 in response to a defined entry point, a defined surgical path, and the anatomical target T. Such parameters may align the flexible surgical device 103 to the defined entry point of the heart muscle and the planned surgical path. The control unit 106 may produce control commands in response to the computed joint motion parameters, which align flexible surgical device 103 to the planned entry point and the planned surgical path; and communicate the robot control commands to surgical robot 101. As such, the control unit 106 through inputs from various components of the surgical robot system 100 is configured to generate guidance commands to correct departures from the desired surgical path defined surgical path to the anatomical target T. Accordingly, departures of the end effector from the surgical path resulting from one or more movements of the handheld introducer can be compensated.

In accordance with a representative embodiment, the guidance signals (or guidance commands) are generated by the processor 130 and based on various inputs from the tracking system 120, or the image acquisition device 112, or both. Illustratively, the guidance commands and other control processes are generated by the processor 130 of control unit 106 in connection with data in memory 132 and software instantiated in the memory 132. Alternatively, these guidance commands and other control processes may be implemented by modules that are embodied by any combination of hardware, software and/or firmware installed on any platform such as a general computer, application specific integrated circuit (ASIC), FPGA, or processor.

Figures 4A, 4B:
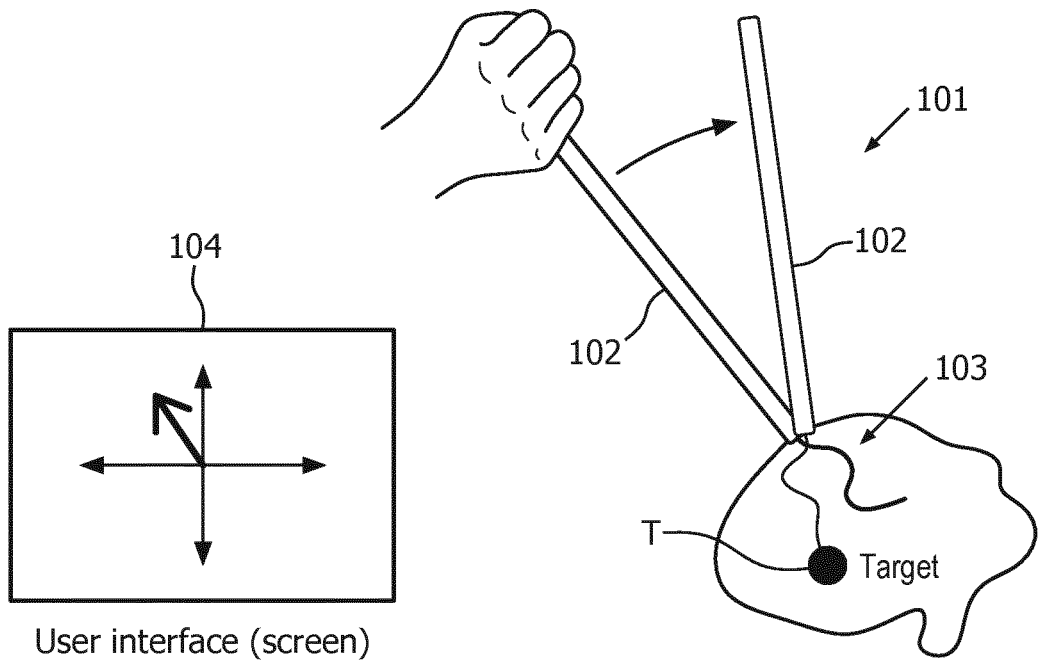
FIGS. 4A and 4B are schematic diagrams illustrating a guidance mode of the surgical robot of the system of FIG. 1A.

In a position guidance mode, if the kinematics of the flexible surgical device 103 are insufficient to move to the target T, assistance or instructions can be provided to the user to inform them how to move the handheld introducer 102 so that the flexible surgical device 103 can reach desired target T. The assistance or instructions for guided motion of the handheld introducer 102 can be conveyed visually, such as an arrow displayed via the display 104, for example as shown in FIGS. 4A and 4B, where the display 104 can either be a typical display in the operating room or a device mounted display associated with the surgical robot 101. The assistance or instructions may also be given by any known output device including visual such as graphical displays or indicator lights, audible cues, such as beeps or tones, or tactile cues, such as vibrations. In such embodiments, the clinician is guided by instructions. Based on these instructions, the clinician is guided to move the handheld introducer 102 on the outside of the patient P to reach a deployment position (e.g., the location where the valve is to be replaced) inside the patient P, and the flexible surgical device 103 is then controlled to adjust its shape or position to reach the deployment position.

In certain embodiments, the instructions for guiding the clinician are generated by the processor 130 and based on various inputs from the tracking system 120, or the image acquisition device 112, or both. To this end, the instructions and other control processes are generated by the processor 130 of control unit 106 in connection with data in memory 132 and software instantiated in the memory 132. Alternatively, these guidance instructions and other control processes may be implemented by modules that are embodied by any combination of hardware, software and/or firmware installed on any platform such as a general computer, application specific integrated circuit (ASIC), FPGA, or processor.

Representative embodiments also are directed to a non-transitory computer-readable storage medium having stored therein machine readable instructions configured to be executed by the processor 130 to control the surgical robot system 100 including the surgical robot 101 having the handheld introducer 102 to be positioned at an entry to a patient's body and the flexible surgical device 103 to be positioned at a surgical site S within the patient's body. Illustratively, the machine readable instructions are stored in memory 132 and, in connection with processor 130 and other components of the surgical robot system 100, are configured to perform a method 500 to compensate for motion of the handheld introducer 102.

Figure 5:
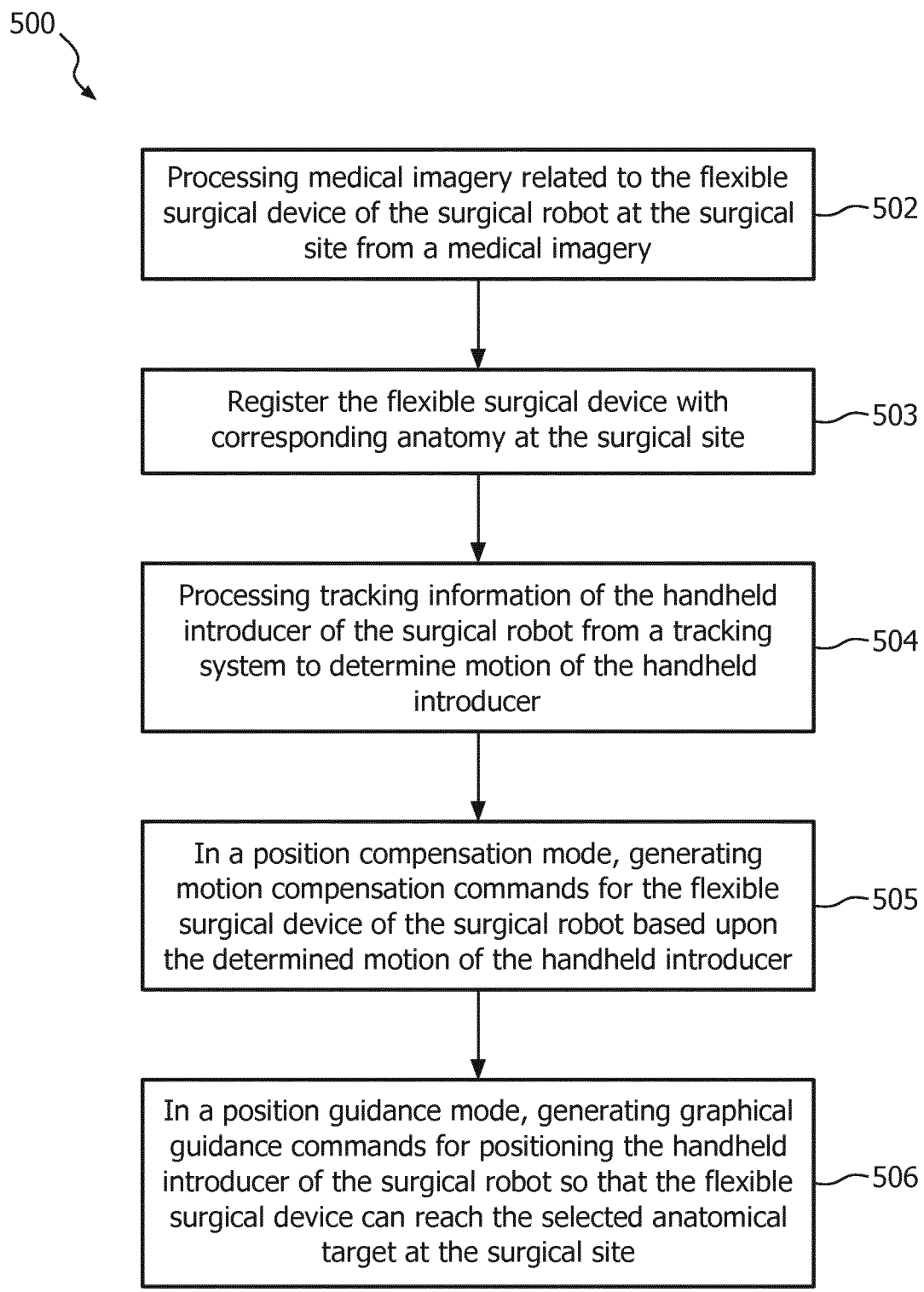
FIG. 5 is a flowchart illustrating various steps in a method of controlling the surgical robot in accordance with features of a representative embodiment.

FIG. 5 is a flowchart illustrating major operations of one embodiment of a method 500 of control and guidance which may be performed by the surgical robot system 100. In the description below, to provide an example it will be assumed that method 500 is performed by the version of surgical robot system 100 which is illustrated in FIG. 1A.

With additional reference to FIGS. 4A, 4B and 5, the method 500 includes operation 502 which includes processing medical imagery related to the flexible surgical device 103 of the surgical robot 101 at the surgical site S from a medical imagery device such as the image acquisition device 112. An image related to the flexible surgical device 103 is taken using an image acquisition device 112, as discussed above.

Operation 503 includes registering the flexible surgical device 103 with corresponding anatomy at the surgical site S based upon the medical imagery that is processed in operation 502. The shape and pose of the flexible surgical device 103, and/or registration within the surgical site S, is determined using the approaches discussed above. For example, real-time tracking of surgical tools relative to a pre-operative surgical plan and intra-operative images involving an image-based registration and tool tracking registration are disclosed in commonly owned U.S. Patent Application Publication 2012/0294498, the entire disclosure of which is specifically incorporated herein by reference. Since anatomy is visible in the image, relative position of the flexible surgical device 103 with respect to the anatomy is also known and the flexible surgical device 103 can be used to reach an anatomical target T using the computed position and the control unit 106.

Operation 504 includes processing tracking information of the handheld introducer 102 of the surgical robot 101 from a tracking system 120 to determine motion of the handheld introducer 102. Tracking system 120 is configured to generate tracking information with respect to the handheld introducer 102 of the surgical robot 101. The tracking system 120 may be one or more of an optical tracking system, mechanical tracking system, and electromagnetic tracking system. A sensor or tag could be included at the handheld introducer 102 of the surgical robot 101 to cooperate with the tracking system 120.

The method 500 includes, in a position compensation mode 505, generating motion compensation commands for the flexible surgical device 103 of the surgical robot 101 based upon the determined motion of the handheld introducer 102. Thus, to keep the flexible surgical device 103 in the same position for the duration of procedure, such as a biopsy or heart ablation, the control unit 106 will regularly or continuously update the position thereof using tracking information of the handheld introducer 102 of the surgical robot 101 from the tracking system 120. So, the flexible surgical device 103 is controlled to move inside the patient to compensate for free-hand motion of the handheld introducer 102 on the outside of the patient.

In certain embodiments, the method 500 may further include transmitting the medical imagery to a display 104. The display arrangement is broadly defined herein as any device structurally configured for displaying images and tracked surgical tools under any suitable technique. Examples of a display include a computer monitor, a television screen, a touch screen, a projector, and Head-mounted display (HMD).

In certain embodiments, the method 500 may further include processing a selection input from a user interface 110 for selection of an anatomical target T at the surgical site S by the user. Thus, a clinician may be prompted via the display 104 to select an anatomical target T or otherwise select a surgical path to the target T. As such, the clinician may select the anatomical target T via the user interface 110, such as a keyboard, mouse or touch screen, for example.

And, in a position guidance mode 506, the method 500 may include generating guidance commands (e.g. FIG. 4A) for positioning the handheld introducer 102 of the surgical robot 101 so that the flexible surgical device 103 can reach the selected anatomical target T at the surgical site S. In certain embodiments, the desired motion of the handheld introducer 102 can be displayed via the display 104, e.g. as shown in FIGS. 4A and 4B. So, the clinician is guided by instructions to move the handheld introducer 102 on the outside of the patient P, to reach a deployment position inside the patient P, and the flexible surgical device 103 is then controlled to adjust the shape or position thereof In certain embodiments, the method further comprises processing an activation signal from a user interface 110 to activate the position compensation mode after completion of the position guidance mode. Thus, a clinician may be prompted via the display 104 to select the position compensation mode after the position guidance mode is complete. As such, the clinician may select the appropriate mode via the user interface 110, such as keyboard, mouse or touch screen, for example, as noted above.

In certain embodiments, the medical imagery is generated with a medical imagery device such as image acquisition device 112, including at least one of an X-ray device, computed tomography (CT) device, ultrasound sensor (US) and an endoscope. As discussed above, in certain embodiments, the tracking information is generated with a tracking system 120 including at least one of an optical tracking system, mechanical tracking system, and electromagnetic tracking system.

The present teachings are part of a technological progression towards smart systems and devices. Possible applications include augmented reality of live video with preoperative CT, surgical navigation, especially in minimally invasive surgery where the workspace is obscured from view, and finding anatomical targets and tumors.

While this disclosure describes control of the surgical robot 101 in the context of endoscopic procedures, the method is applicable to procedures using other imaging for example, ultrasound, or shape sensing such as optical shape sensing, infrared range sensing, and other modalities as well.

In view of this disclosure it is noted that the various components of the surgical system and surgical robot of the present teachings can be implemented in a variety of devices, hardware, firmware, software, standards and protocols. Further, the various devices, hardware, firmware, software, standard and protocols are included by way of example only and not in any limiting sense. In view of this disclosure, those skilled in the art can implement the present teachings in determining their own applications and needed devices, hardware, firmware, software, standard and protocols, while remaining within the scope of the appended claims.

What is claimed is:

1. A surgical robot system comprising:
a flexible surgical device;
a handheld introducer configured to facilitate introduction of the flexible surgical device;
an image acquisition device configured to capture one or more images of the flexible surgical device, the images being indicative of at least one of: a shape, a pose, and a position of the flexible surgical device;
a tracking system configured to track a position of at least one point on the handheld introducer; and
a processor configured to generate guidance commands to control the flexible surgical device based on information relating to the images of the flexible surgical device and the position of at least one point of the handheld introducer.

2. The surgical robot system of claim 1, wherein the flexible surgical device comprises at least one of the following: (i) a two-linkages, one joint device, (ii) a snake-like robot, and (iii) a steerable catheter.

3. The surgical robot system of claim 1, wherein the flexible surgical device comprises an end-effector coupled to a distal end.

4. The surgical robot system of claim 3, wherein the processor is further configured to generate guidance commands to move and position the end-effector to or near a target location.

5. The surgical robot system of claim 4, wherein, in a position compensation mode, the processor is configured to generate guidance commands to correct departures of the end effector from a surgical path resulting from one or more movements of the handheld introducer.

6. The surgical robot system according to claim 1, wherein the image acquisition device comprises at least one of an X-ray device, computed tomography (CT) device, ultrasound sensor (US), and an endoscope.

7. The surgical robot system according to claim 1, wherein the tracking system comprises at least one of an optical tracking system, mechanical tracking system, and electromagnetic tracking system.

8. The surgical robot system according to claim 1, wherein the processor is further configured to generate commands based on a changed position or orientation of the handheld introducer.

9. The surgical robot system according to claim 1, further comprising a display configured to display the images.

10. The surgical robot system according to claim 9, wherein the processor is further configured to generate commands indicative of another position or orientation of the handheld introducer and the display is configured to display images based on the commands.

11. A control unit for a surgical robot system comprising a flexible surgical device and a handheld introducer configured to facilitate introduction of the flexible surgical device, the control unit comprising:
a processor configured to:
receive, from an image acquisition device, one or more images of the flexible surgical device, the images being indicative of at least one of:
a shape, a pose, and a position of the flexible surgical device;

receive, from a tracking system, tracking information indicative of a position of at least one point on the handheld introducer; and generate guidance commands to control the flexible surgical device based on information relating to the images of the flexible surgical device and the position of the at least one point of the handheld introducer.

12. The control unit according to claim 11, wherein the flexible surgical device comprises an end-effector; and the processor is further configured to generate guidance commands to move and position the end-effector to or near a target location, and wherein, in a position compensation mode, the processor is further configured to generate guidance commands to correct departures of the end effector from a surgical path resulting from one or more movements of the handheld introducer.

13. The control unit according to claim 11, wherein the processor is further configured to:

receive a selection input from a user interface for selection of an anatomical target at a surgical site by a user; and in a position guidance mode, based on the selection input, generate guidance commands for positioning the handheld introducer of the surgical robot system so that the flexible surgical device reaches the selected anatomical target at the surgical site.

14. The control unit according to claim 13, wherein the processor is further configured to receive an activation signal from a user interface, and, based on the activation signal, to activate a position compensation mode after completion of the position guidance mode.

15. The control unit according to claim 11, wherein the processor is further configured to process medical imagery of the flexible surgical device at a surgical site from a medical imagery device comprising at least one of an X-ray device, computed tomography (CT) device, ultrasound sensor (US) and an endoscope.

16. A non-transitory computer-readable storage medium having stored therein machine readable instructions configured to be executed by a processor to control a flexible surgical device and a handheld introducer configured to facilitate introduction of the flexible surgical device at a surgical site, the machine readable instructions, when executed by the processor, cause the processor to:

receive, from an image acquisition device, one or more images of the flexible surgical device, the images being indicative of at least one of:

a shape, a pose, and a position of the flexible surgical device;

receive, from a tracking system, tracking information indicative of a position of at least one point on the handheld introducer; and generate guidance commands to control the flexible surgical device based on information relating to the images of the flexible surgical device and the position of the at least one point of the handheld introducer.

17. The non-transitory computer-readable storage medium according to claim 16, wherein, when executed by the processor, further cause the processor to:

receive a selection input from a user interface for selection of an anatomical target at the surgical site by a user; and in a position guidance mode, based on the selection input, generate guidance commands for positioning the handheld introducer of a surgical robot so that the flexible surgical device reaches the selected anatomical target at the surgical site.

18. The non-transitory computer-readable storage medium according to claim 16, wherein, when executed by the processor, further cause the processor to process an activation signal from a user interface to activate a position compensation mode after completion of a position guidance mode.

19. The non-transitory computer-readable storage medium according to claim 16, wherein the images are generated with a medical imagery device comprising at least one of an X-ray device, computed tomography (CT) device, ultrasound sensor (US) and an endoscope.

* * * * *